United States Patent
Koh et al.

(10) Patent No.: US 7,636,599 B1
(45) Date of Patent: Dec. 22, 2009

(54) DETERMINING PATIENT POSTURE FROM SENSED CARDIAC DATA

(75) Inventors: Steve Koh, South Pasadena, CA (US); Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 271 days.

(21) Appl. No.: 11/626,301

(22) Filed: Jan. 23, 2007

(51) Int. Cl.
*A61N 1/00* (2006.01)

(52) U.S. Cl. ........................................ 607/17

(58) Field of Classification Search ............... 607/9–29
See application file for complete search history.

(56) References Cited

U.S. PATENT DOCUMENTS 6,975,904 B1 * 12/2005 Sloman ..................... 607/28

\* cited by examiner

*Primary Examiner*—Scott M Getzow

(57) ABSTRACT

Exemplary techniques for determining patient posture from cardiac data sensed by an implantable medical device (IMD) are described. One technique involves sensing intracardiac electrogram (IEGM) data from a patient and determining a posture of the patient from the sensed IEGM data. The technique then considers the posture in formulating patient therapy.

14 Claims, 7 Drawing Sheets

DETERMINING PATIENT POSTURE FROM SENSED CARDIAC DATA

FIELD OF THE INVENTION

The subject matter presented herein generally relates to implantable medical devices (IMDs) and determining patient posture from cardiac data sensed by the IMD.

BACKGROUND

Many implantable medical devices (IMDs) employed in a cardiac context gather or sense cardiac data, such as intracardiac electrogram (IEGM) data, to achieve their functionality. For instance, an IMD functioning as a pacemaker senses IEGM data. The IMD then analyzes the IEGM data to detect various parameters. Some IMDs employ various posture sensors, such as accelerometers, to provide information about a posture of the patient. The parameters and the posture information are utilized by IMD algorithms to effect pacing therapy and/or other cardiac conditions. IMDs by nature have finite processing resources and need to be ultra-reliable. Traditional posture sensors add an additional level of complexity to the IMD and hence a potential point of failure. Further, processing information from the posture sensors is resource intensive. In contrast, deriving additional information, such as posture information, from the sensed cardiac data would result in a relatively simpler IMD that utilizes a relatively lower amount of IMD resources.

SUMMARY

Exemplary techniques for determining patient posture from cardiac data sensed by an implantable medical device (IMD) are described. One technique involves sensing intracardiac electrogram (IEGM) data from a patient and determining a posture of the patient from the sensed IEGM data. The technique then considers the posture in formulating patient therapy.

BRIEF DESCRIPTION OF THE DRAWINGS

Features and advantages of the described implementations can be more readily understood by reference to the following description taken in conjunction with the accompanying drawings.

DETAILED DESCRIPTION

Figure 1:
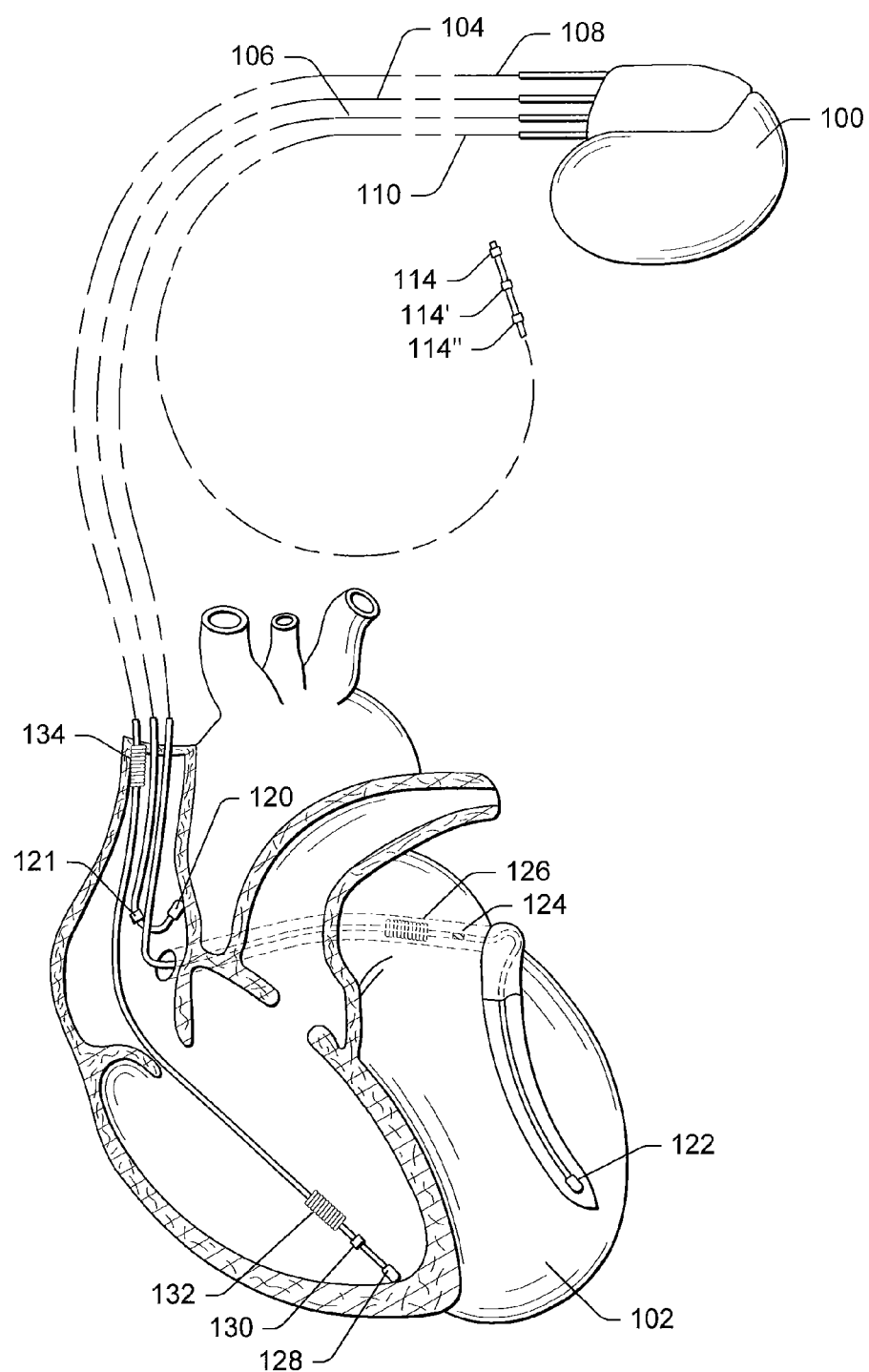
FIG. 1 is a simplified diagram illustrating an exemplary implantable IMD operable to determine patient posture from cardiac data sensed by the IMD in accordance with one embodiment.

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements wherever feasible.

OVERVIEW

Various exemplary techniques, methods, devices, systems, etc., described herein pertain to determining patient posture from sensed cardiac data. Sensed cardiac data, in the form of IEGM data, is gathered by implantable medical devices (IMDs) employed in a cardiac context to record electrical activity of the heart. Various parameters can be derived from the IEGM data. These parameters can be indicative of a cardiac condition associated with the heart's electrical activity. In addition to the traditional uses of IEGM data, the parameters can be further analyzed to yield information about the patient's posture and/or posture changes.

One technique establishes a baseline or first patient posture during which IEMG data is sampled. For instance, a baseline can be established when an activity sensor of the IMD indicates a long period of very low activity. Such periods are generally associated with sleeping. The technique then operates on the presumption that the patient is lying generally horizontally during the period. Parameter values from the first patient posture can then be utilized as a baseline for comparison to IEMG data sampled at other times. Changes in various IEGM parameters can be indicative of the patient assuming different postures. For example, a Dmax parameter has been found to increase approximately 16% with a patient posture change from supine to standing, while a peak-to-peak (P-P) parameter increased 10% under the same conditions. Various examples and discussion below elaborate on these concepts.

The ability to distinguish among various patient postures by analyzing the IEGM data offers further opportunity to alter patient therapy based upon the patient's posture. In one case, specific patient therapies can be inhibited in instances where the therapy may, for example, cause the patient to lose their balance. In one such case, delivering a shock to a standing patient may cause the patient to lose their balance and fall. Shocking therapy can therefore be inhibited until the patient changes to a more suitable posture. Other examples are described below.

The described implementations can utilize IEGM data, which is often already sensed for other purposes, to determine patient posture and/or posture changes. Such techniques utilize relatively low amounts of the IMD's resources. Some techniques offer further resource savings by selectively analyzing IEGM data corresponding to periods of increased patient activity, thereby eliminating processing of IEGM data that is unlikely to reveal a posture change.

Exemplary IMD

The techniques described below are optionally implemented in connection with any IMD that is configured or configurable to sense cardiac data.

FIG. 1 shows an exemplary IMD 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves, non-myocardial tissue, other nerves, etc. In addition, the device 100 includes a fourth lead 110 having, in this implementation, three electrodes 114, 114', 114" suitable for stimulation of autonomic nerves, non-myocardial tissue, other nerves, etc. For example, this lead may be positioned in and/or near a patient's heart or near an autonomic nerve within a patient's body and remote from the heart. In another example, the fourth lead can be configured to sense the phrenic nerve and/or activation of the diaphragm. The right atrial lead 104, as the name implies, is positioned in and/or passes through a patient's right atrium. The right atrial lead 104 optionally senses atrial cardiac signals and/or provides right atrial chamber stimulation therapy. As shown in FIG. 1, the IMD 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves, non-myocardial tissue, other nerves, etc. In an alternative configuration, lead 110 can be replaced with a mechanism for connecting the IMD to various other devices. For example, the mechanism can facilitate connecting IMD 100 to a drug pump for dispensing drugs into the patient in accordance with instructions received from the IMD. The skilled artisan should recognize various other configurations that may be employed which are consistent with the principles described above and below.

To sense atrial cardiac signals, ventricular cardiac signals and/or to provide chamber pacing therapy, particularly on the left side of a patient's heart, the IMD 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

IMD 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

Figure 2:
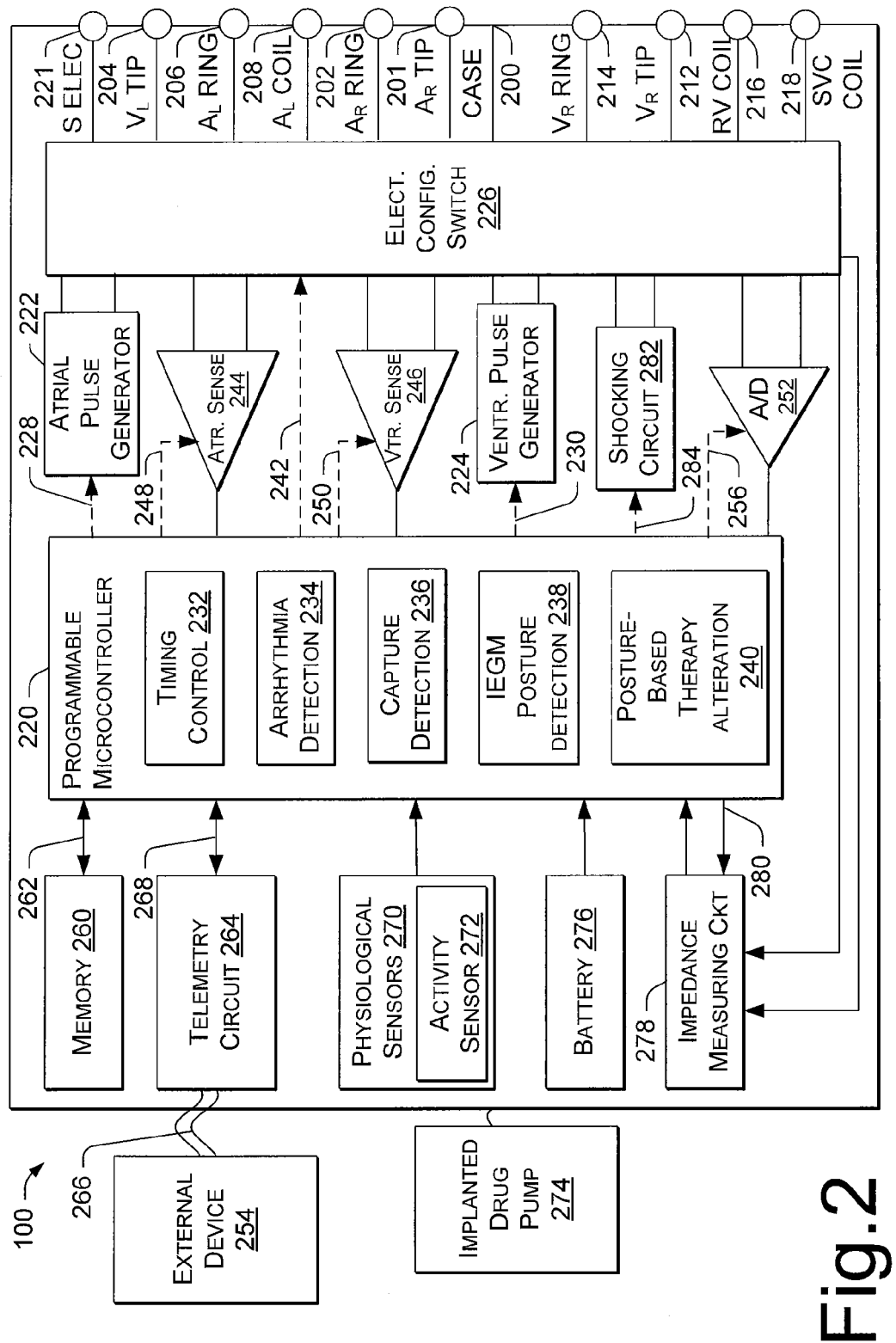
FIG. 2 is a functional block diagram of an exemplary implantable IMD illustrating basic elements that are operable to determine patient posture from cardiac data sensed by the IMD in accordance with one embodiment.

FIG. 2 shows an exemplary, simplified block diagram depicting various components of IMD 100. The IMD 100 can be capable of treating both fast and slow arrhythmias with stimulation therapy, including cardioversion, defibrillation, and pacing stimulation. The IMD can be solely or further capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable IMD. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 200 for IMD 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 201 adapted for connection to the atrial tip electrode 120. A right atrial ring terminal ($A_R$ RING) 202 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

At the core of the IMD 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller(s) 220 may be used that carries out the functions described herein.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detection module 234, a capture detection module 236, an IEGM posture detection module 238, and a posture-based therapy alteration module 240. The IEGM posture detection module 238 is operable to determine patient posture from sensed IEGM data. The arrhythmia detection module 234, capture detection module 236, and IEGM posture detection module 238 can be utilized by the IMD 100 for detecting patient conditions. The posture-based therapy alteration module 240 offers a mechanism to determine desirable times to administer various therapies such as pacing, defibrillation and/or in vivo dispensing of pharmaceuticals in consideration of the patient's posture. The aforementioned components may be implemented in hardware as part of the microcontroller 220, or as software/firmware instructions programmed into the device and executed on the microcontroller 220 during certain modes of operation.

In this configuration, among other functions, the posture-based therapy alteration module 240 operates as an orthostatic compensator. The orthostatic compensator can in various instances, such as when the patient stands up, provide responsive therapies including increasing a pacing rate. In other instances, the posture-based therapy altering module 240 operates on patient therapies in other manners. For instance, in a scenario where shocking therapy is to be delivered, the posture-based therapy alteration module 240 can operate to inhibit the delivery of the shocking therapy if the patient is in a standing posture to avoid potentially causing the patient to fall and injure him/herself. Other configurations may perform similarly if the patient is in a sitting posture to avoid, for instance, the potential of shocking a patient who is driving a car.

In the illustrated configuration, the posture-based therapy alteration module 240 is illustrated as a software/firmware logical component associated with microcontroller 220. In other scenarios, the posture-based therapy alteration module could be a self-contained or standalone component, such as a hardware component that performs its own processing. The skilled artisan should recognize other configurations that are consistent with the concepts described above and below.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the IMD 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or a data acquisition system (introduced below) to determine or detect whether capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, IMD 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detection module 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

The IEGM posture detection module 238 can further analyze some or all of the cardiac signals sensed by the atrial and ventricular sensing circuits, 244 and 246 to determine the patient's posture at the time particular cardiac signals are sensed. In some configurations, the posture detection module 238 receives activity data from one or more activity sensors (introduced below) and analyzes a corresponding sub-set of sampled cardiac signals. For instance, the IEGM posture detection module 238 can analyze only the cardiac signals associated with instances when patient activity exceeds a predetermined value. In such configurations processing resources are saved for those instances where the patient's physical activity level is sufficiently high to be associated with a posture change. Various implementations will, of course, strike different balances in regards to the predetermined value. For instance, a relatively low predetermined value can allow detection of a higher percentage of posture changes whereas a higher predetermined value can conserve processing resources.

Cardiac signals are also applied to inputs of an analog-to-digital (A/D) data acquisition system 252. The data acquisition system 252 is configured to acquire intracardiac electrogram (IEGM) signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve or other tissue stimulation lead 110 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The IMD 100 can further include a physiologic sensor(s) 270 to detect one or more of patient activity and respirations, among others. In this instance, the physiologic sensors include at least an activity sensor 272. Among other uses, activity sensor 272 can provide patient activity data that can be utilized by IEGM posture detection module 238 to detect patient posture changes. Further, microcontroller 220 can utilize data received from the physiologic sensor(s) 270 to adjust the various pacing parameters (such as rate, AV Delay, VV Delay, etc.) at which the atrial and ventricular pulse generators, 222 and 224, generate stimulation pulses.

While shown as being included within the IMD 100, it is to be understood that the physiologic sensor 270 may also be external to the IMD 100, yet still be implanted within or carried by the patient. Examples of physiologic sensors that may be implemented in device 100 include known sensors that, for example, sense pressure, respiration rate, pH of blood, ventricular gradient, cardiac output, preload, afterload, contractility, oxygen levels, and so forth.

IMD 100 may also include, or be in communication with, an implanted drug pump 274 or other drug delivery mechanism to effect patient therapy. The drug pump can be activated in various scenarios, and operation thereof can be altered or controlled by posture-based therapy altering module 240.

The IMD 100 additionally includes a battery 276 that provides operating power to all of the circuits shown in FIG. 2. For the IMD 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The IMD 100 can further include magnet detection circuitry (not shown), coupled to the microcontroller 220, to detect when a magnet is placed over the IMD 100. A magnet may be used by a clinician to perform various test functions of the IMD 100 and/or to signal the microcontroller 220 that the external programmer 254 is in place to receive or transmit data to the microcontroller 220 through the telemetry circuits 264.

The IMD 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds (HF indications—pulmonary edema and other factors); detecting when the device has been implanted; measuring stroke volume; and detecting the opening of heart valves, etc. The impedance measuring circuit 278 is advantageously coupled to the switch 226 so that any desired electrode may be used.

In the case where the IMD 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. Examples of how the microprocessor's posture-based therapy alteration module 240 can influence therapy delivery are described below in relation to the FIGS. 6-7.

The shocking circuit 282 generates shocking pulses in a range of joules, for example, conventionally up to about 40 J, as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In low-energy cardioversion, an IMD typically delivers a cardioversion stimulus (e.g., 0.1 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the IMD initiates defibrillation therapy.

While an IMD may reserve defibrillation as a latter tier therapy, it may use defibrillation as a first-tier therapy for VF. In general, an IMD does not synchronize defibrillation therapy with any given portion of an ECG. Again, defibrillation therapy typically involves high-energy shocks (e.g., 5 J to 40 J), which can include monophasic or unidirectional and/or biphasic or bidirectional shock waveforms. Defibrillation may also include delivery of pulses over two current pathways.

Exemplary Posture Detection Techniques from IEGM Data

Figure 3:
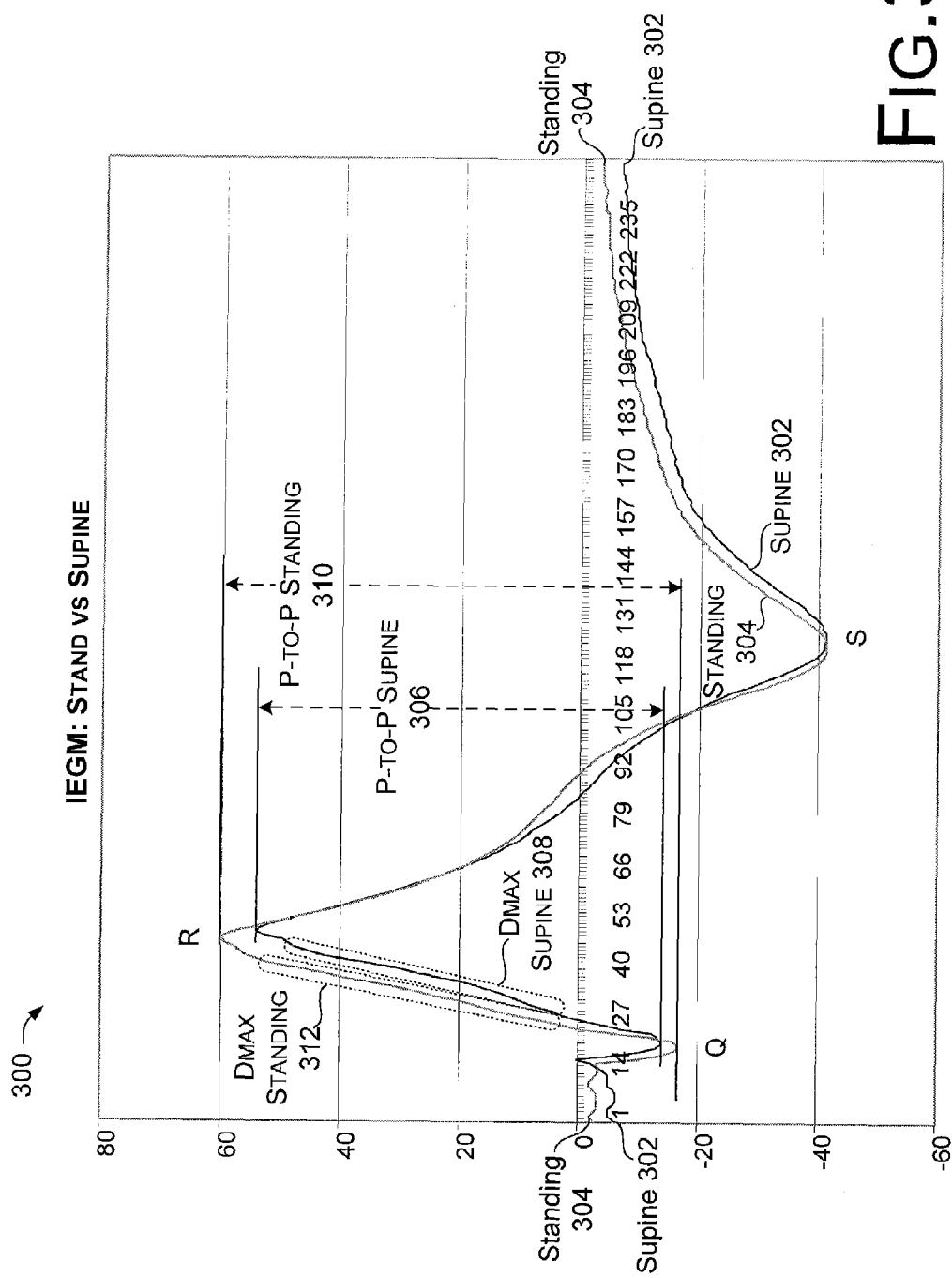
FIG. 3 is a plot of superimposed IEGM data that can be utilized to determine patient posture in accordance with various embodiments.
Figure 4:
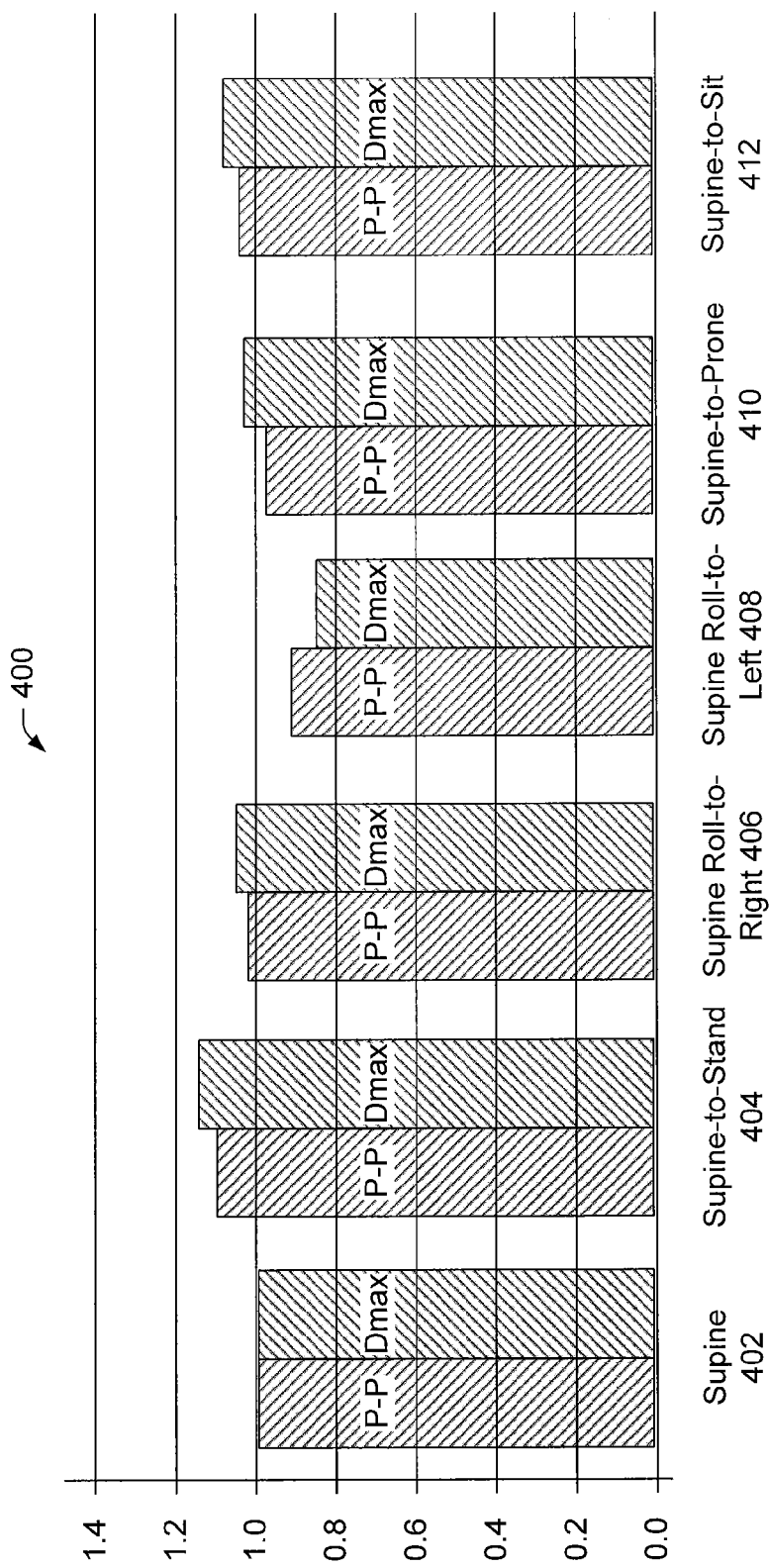
FIG. 4 is a chart that correlates IEGM parameter values in accordance with various embodiments.
Figure 5:
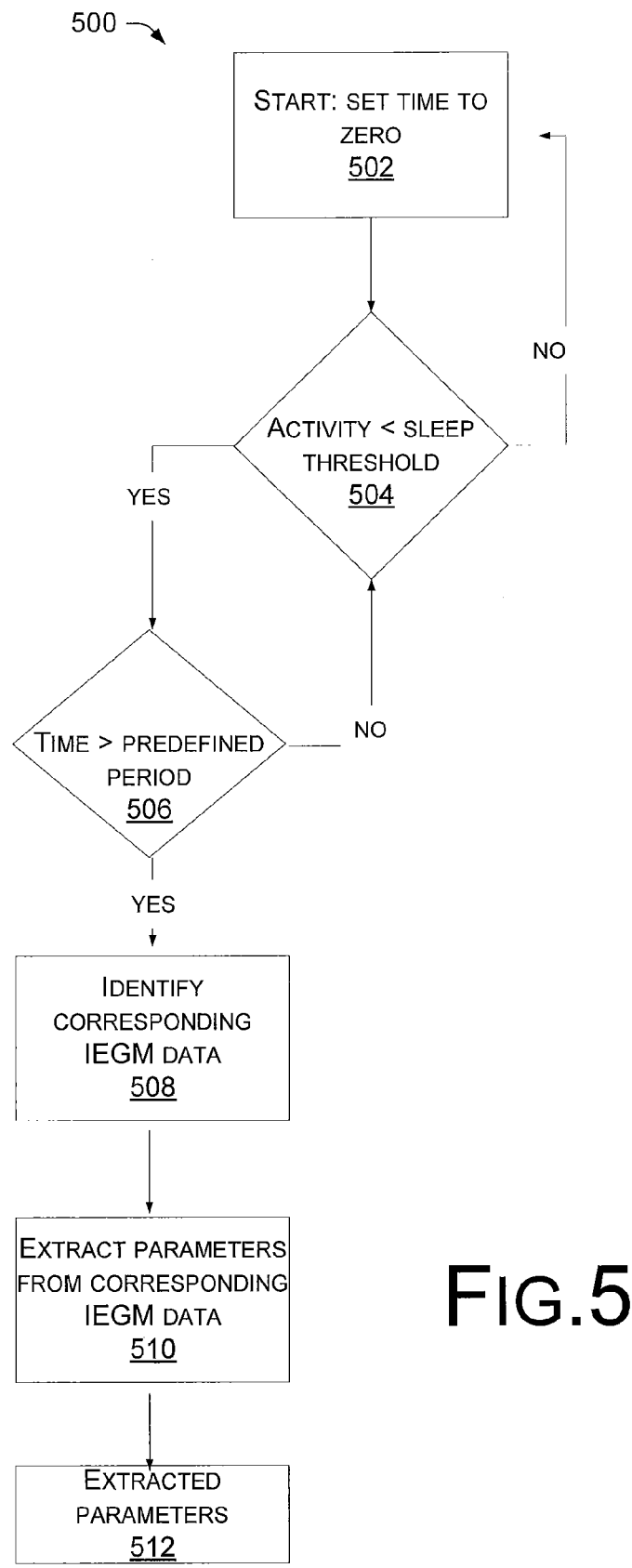
FIG. 5 is a flowchart of an exemplary technique for establishing a baseline patient posture in accordance with one embodiment.

FIGS. 3-5 illustrate examples for detecting posture changes from IEGM data.

FIG. 3 represents a plot 300 of sensed IEGM data. In the case of plot 300, two QRS complexes from a patient's IEGM data are superimposed over one another for discussion purposes. Line 302 represents a QRS complex sensed from a patient in a supine posture. Line 304 represents a QRS complex sensed from the patient in a standing posture. Changes to various parameters of the sensed IEGM data can be determinative of patient posture. For example, two such determinative parameters are peak-to-peak (P-to-P) and Dmax. In relation to an individual QRS complex, P-to-P represents the distance between the lowest value of the descending Q-wave peak and the highest value of the ascending R-wave peak. Dmax is the measured value of the slope of the ascending transition from the Q-wave to the R-wave. In this instance, for supine posture (i.e., line 302), P-to-P is designated at 306 and Dmax is designated at 308. For standing posture (i.e., line 304), P-to-P is designated at 310 and Dmax is designated at 312.

In relation to plot 300, standing Dmax 312 is 15.7% greater than supine Dmax 308. Similarly, standing P-to-P 310 is 10.1% greater than supine P-to-P 306. In summary, FIG. 3 provides examples of how parameter values from sensed IEGM data can be indicative of the patient's posture relative to supine and standing postures. In a general sense, various parameters of the sensed IEGM data can be determinative of patient posture and/or posture changes. For example, if the data indicates a posture change from supine to standing, then the data also indicates that the current posture is standing. In some cases, it can be more useful to detect posture changes, while in other cases it can be more useful to determine a patient's posture at a given point in time. For instance, in an orthostatic hypotension scenario it may be more useful to detect a situation where the patient is in the process of standing-up (i.e., posture change) so that therapy can be provided to alleviate or reduce an onset of orthostatic hypotension. In another instance, such as a defibrillation scenario, determining the patient's posture and avoiding shocking when the patient is standing, can be more valuable than detecting posture changes. The concepts described herein can be utilized to detect posture changes and/or to determine the patient's posture (whether or not posture change is occurring) from sensed IEGM data.

Exemplary IEGM Data Analysis

FIG. 4 is a chart 400 that correlates IEGM parameter values to patient posture changes from a known or starting posture. In this example the starting posture is supine, though other postures such as standing, sitting, or prone could serve as the starting point. The starting supine posture and the posture changes are listed along the horizontal axis of chart 400 and designated respectively as supine 402, supine-to-standing 404, supine roll-to-right 406, supine roll-to-left 408, supine-to-prone 410, and supine-to-sitting 412. The descriptive names assigned to the posture changes convey the activity. For instance, supine roll-to-right 406 constitutes a posture change from supine to the patient lying on his/her right side and correspondingly, supine roll-to-left 408 constitutes a posture change from supine to the patient lying on his/her left side. Parameter values are affected by various physiological factors during posture change. For example, as a person stands, blood is moved out of the cardiac chamber at an increased rate due to gravity. Accordingly, the heart becomes more compact and experiences increased electrical density. Conversely, in the case of supine roll-to-left 408 stretching of the cardiac muscle can cause more interstitial space between the cardiac cells and therefore decreased electrical density.

In this instance, the tracked parameters are P-P and Dmax which are introduced above in relation to FIG. 3. As mentioned above, other parameters can be tracked to detect posture changes. In this case, parameter values for the starting supine posture 402 and each posture change 404-412 are represented along the vertical axis. Individual parameter values ascend to a relative value as indicated along the vertical axis. In this instance, the parameter values of the posture changes 404-412 are normalized to the supine posture 402. Accordingly, the P-P and Dmax values for the supine posture 402 are assigned a relative value of 1.0. Parameter values for the posture changes are expressed relative to the supine posture 402. Chart 400 offers an example of analyzing IEGM data to detect patient posture changes. In this specific example the posture changes are detected via normalization to the baseline parameter values. A calibration technique for establishing a base line patient posture is described below in relation to FIG. 5.

Exemplary Posture Calibration Techniques

FIG. 5 relates to a calibration technique or method 500 for establishing a starting or baseline patient posture. Establishing the baseline allows subsequent posture changes to be detected from IEGM data as is described above in relation to FIG. 4 and as will be described in more detail below in relation to FIG. 6. The order in which the technique is described is not intended to be construed as a limitation, and any number of the described blocks can be combined in any order to implement the technique, or an alternate technique. Furthermore, in some instances, the technique can be implemented in any suitable hardware, software, firmware, or combination thereof employed by a computing device such as an implantable medical device (IMD). In such a scenario, the method can be stored as a set of instructions on a computer readable media for execution by the computing device.

Calibration technique 500 is a technique for establishing the patient's posture during a period of low activity (i.e., not undergoing a posture change). Technique 500 may be implemented in connection with any suitably configured implantable medical devices (IMDs) and/or systems such as those described above. Technique 500 includes blocks 502-512.

Calibration technique 500 starts at block 502 by setting a time or clock to zero. The patient's activity level is compared to a sleep threshold at 504. If the activity level is less than the threshold (i.e., yes at 504) then the technique proceeds to block 506. If the activity level is greater than the threshold (i.e., no at 504) then the technique returns to block 502 and starts again.

The technique determines whether the time exceeds a predefined period at 506. If the time does not exceed the predefined period (i.e., no at 506) then the technique returns to block 504. If the time does exceed the predefined period (i.e., yes at 506) then the technique proceeds to block 508. Blocks 504 and 506 operate cooperatively to establish periods when the patient is likely sleeping and not moving (i.e., maintaining a given posture). For instance, there may be times when a patient is standing and the patient's activity level is low enough to satisfy block 504. However, the predefined period of block 508 can be assigned a sufficiently long duration that the patient will most likely move before expiration of the time period if the patient is not sleeping. For example, in one case the activity level is sufficiently low to satisfy block 504, so the technique proceeds to block 506. Assume for purposes of explanation that the predefined period is set at one hour. So for one hour the technique cycles between blocks 504 and 506. If at any time in that one hour period the patient moves such that the activity level exceeds the sleep threshold, then the technique returns to block 502 and begins again. Thus, the predefined period can be set to a value which is generally only satisfied during sleep, thereby distinguishing instances such as where the patient is standing but holding still for a short time, from sleep periods where the patient maintains a horizontal posture for a relatively long time.

Once the activity level is maintained below the sleep threshold for the predefined period then the technique identifies corresponding IEGM data at 508. Parameters are extracted from the corresponding IEGM data at 510. FIG. 3 describes but one suitable example for extracting parameters from IEGM data. As discussed in relation to FIG. 4, the extracted parameters 512 can serve as a baseline for detecting subsequent posture changes. Extracted parameters 512 will be utilized further in FIG. 6.

First Exemplary Therapy Alteration

Figure 6:
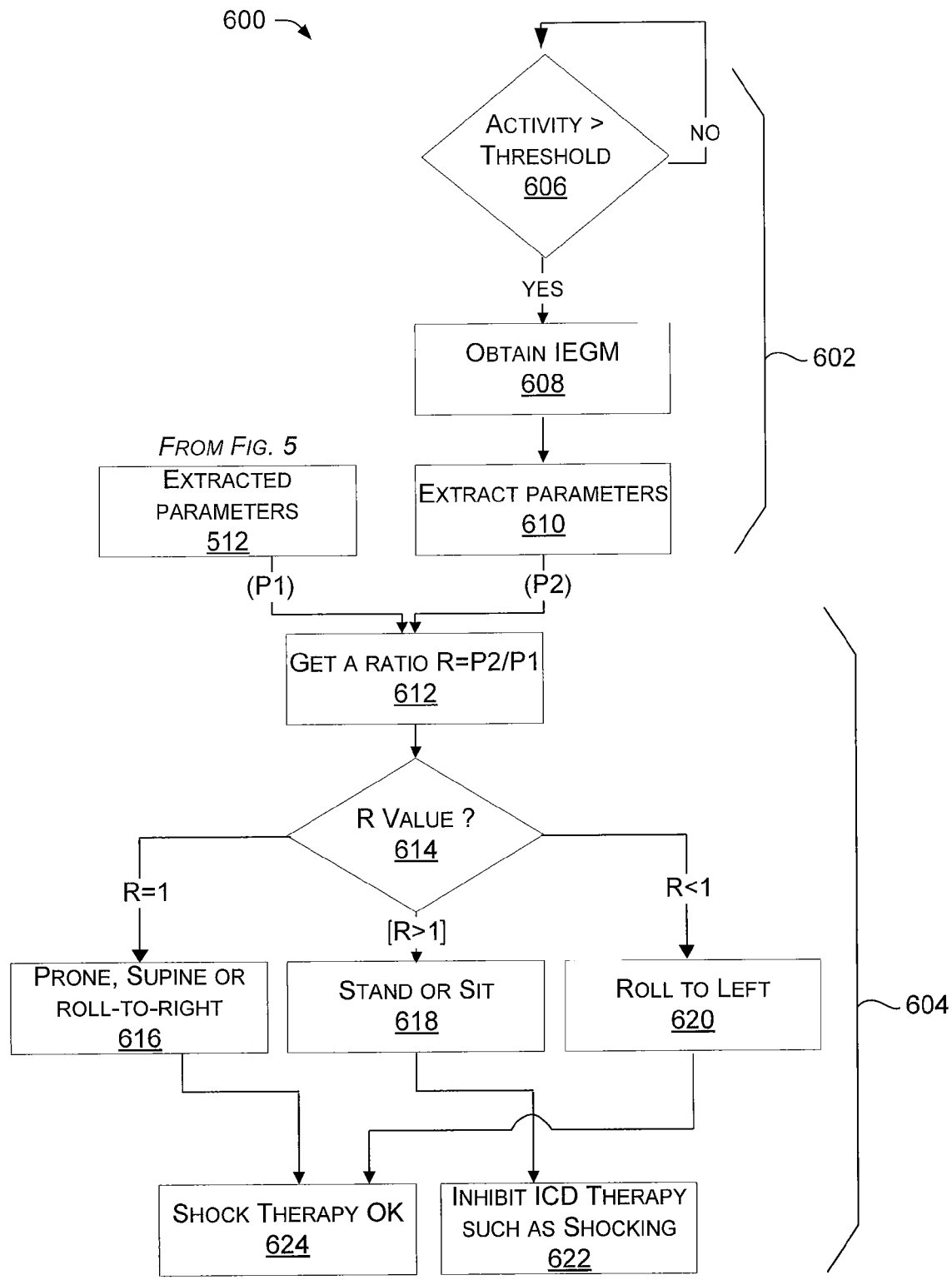
FIGS. 6-7 are exemplary techniques for altering patient therapies based upon IEGM derived patient posture in accordance with one embodiment.

FIG. 6 is a flow diagram of a technique of method 600 for altering patient therapy(s) based upon IEGM derived posture information. Technique 600 includes a first sub-routine 602 which provides IEGM parameters as input to a second sub-routine 604. The second sub-routine also receives parameter input from block 512 which is carried over from FIG. 5. The order in which the technique is described is not intended to be construed as a limitation, and any number of the described blocks can be combined in any order to implement the technique, or an alternate technique. Furthermore, in some instances, the technique can be implemented in any suitable hardware, software, firmware, or combination thereof employed by a computing device such as an implantable medical device (IMD). In such a scenario, the method can be stored as a set of instructions on a computer readable media for execution by the computing device.

First sub-routine 602 starts by determining whether patient activity exceeds a predetermined threshold at 606. In an instance where the activity level exceeds the predetermined threshold (i.e., yes at block 606) then the sub-routine proceeds to block 608. If the activity level is less than the predetermined threshold (i.e., no at block 606) then the sub-routine loops back to block 606. The technique obtains IEGM data for the time when the patient activity exceeds the predetermined threshold at block 608. The technique extracts parameters or parameter values from the obtained IEGM data to detect posture changes. Other implementations can save processing and/or battery resources by employing a CPU interrupt technique so that when the patient activity exceeds the predetermined threshold, a hardware pulse can wake up the CPU rather than the CPU waiting in a round-robin manner for the condition to be satisfied. It is worth noting that block 606 is included in this implementation as a mechanism to conserve IMD processing and battery resources and that the technique can alternatively start at block 608 and simply process most or all sensed IEGM data.

Second sub-routine 604 receives parameters from block 512. These parameters are designated hereinafter as "P1". As described above, parameters P1 are parameter values from a known or baseline posture. In the implementation of FIG. 5, the baseline posture is supine. Sub-routine 604 further receives parameters from the first sub-routine 602. The parameters from the first sub-routine are designated hereinafter as "P2". The second sub-routine receives parameters P1 and P2 and at block 612 determines a ratio ("R") which equals P2 divided by P1 (i.e., R=P2/P1). The ratio R supplies a quantitative comparison of parameter values during the present patient activity (first sub-routine) to the known baseline posture (FIG. 5). Accordingly, a patient posture change can be determined from the R value. The ratio R (or the determined posture) can then be supplied to an algorithm which effects patient therapy. The algorithm can alter one or more patient therapies based upon the R value. In this particular case, in an instance where R=1, then the technique identifies the posture change as one of maintaining supine, supine to prone, or supine roll-to-right at block 616. Alternatively, if R>1 then the technique identifies the posture change as supine to standing or supine to sitting at block 618, and if R<1 then the technique identifies the posture change as supine roll-to-left at block 620.

In this implementation, patient therapy is affected when the posture change results in the patient sitting or standing as is indicated at 618. In such instances certain IMD therapies such as shocking can be inhibited at 622 until a subsequent posture change to a more suitable posture is detected. If the posture change (i.e., R values) indicates other postures such as prone, supine, laying on his/her right or left sides, then patient therapies, such as shock therapies, are unaffected as indicated at 624. Inhibiting shocking and/or other postures when the patient is sitting and/or standing reduces a likelihood of the patient therapy incapacitating the patient in a situation where the patient and/or others could be harmed. For instance, if shock therapy is delivered to a standing patient, the patient may fall over and suffer trauma(s).

Second Exemplary Therapy Alteration

Figure 7:
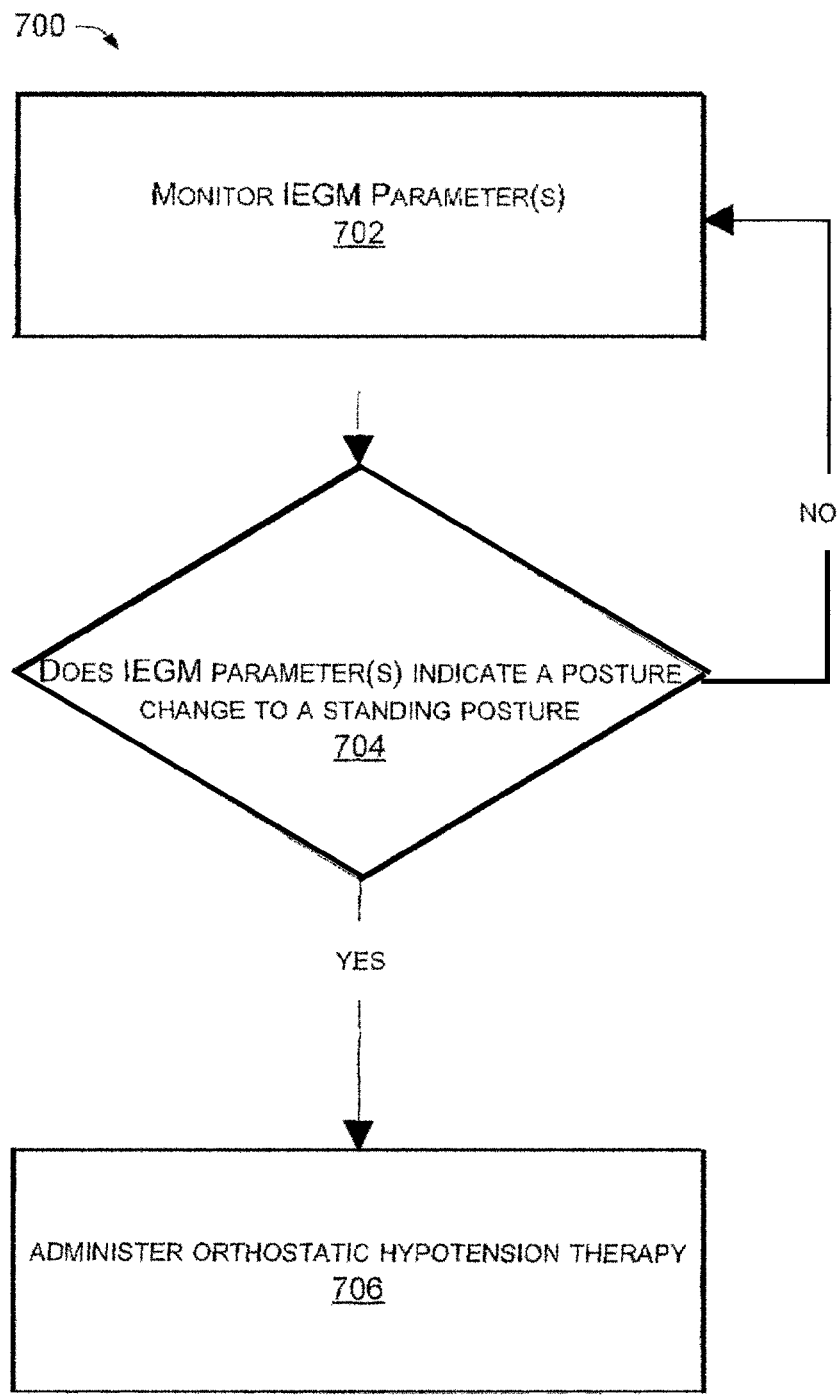

FIG. 7 is a flow diagram of another technique or method 700 for altering patient therapy(s) based upon IEGM derived posture information. The order in which the technique is described is not intended to be construed as a limitation, and any number of the described blocks can be combined in any order to implement the technique, or an alternate technique. Furthermore, in some instances, the technique can be implemented in any suitable hardware, software, firmware, or combination thereof employed by a computing device such as an implantable medical device (IMD). In such a scenario, the method can be stored as a set of instructions on a computer readable media for execution by the computing device.

The technique monitors IEGM parameter(s) at 702. Various IEGM parameters can be indicative of patient postures and/or posture changes. Dmax and P-P are two suitable IEGM parameters which are discussed in detail above. Various implementations can monitor a single parameter and/or multiple parameters of the IEGM data. In some scenarios, the monitored IEGM data and/or other data, such as data obtained from a posture sensor, may be utilized to determine a patient posture at a particular point in time.

At 704, the technique queries whether the IEGM parameter(s) indicates a posture change to a standing posture. Thus, the technique determines whether the patient is changing from the first posture to a second posture, which in this instance is a standing posture. Stated another way, the technique determines from the IEGM data whether the patient has switched or is switching from a non-standing posture, such as supine or sitting, to a standing posture (i.e., the patient is in the act of standing-up or has recently stood-up). In some cases decreased preload to the right atrium as the patient stands will contribute to changes to the IEGM parameters. In an instance where posture change to standing is detected, then the technique proceeds to block 706, otherwise the technique returns to block 702 and continues to monitor the IEGM parameters.

Other variations on this technique can additionally or alternatively be utilized in relation to patient postures. In one scenario it may be sufficient to distinguish patient postures where the patient's thorax is generally vertical (i.e., sitting or standing) from those patient postures where the patient's thorax is generally horizontal (i.e., patient postures other than sitting and standing). For instance, consider again chart 400 of FIG. 4, where in relation to Dmax parameter values, only standing 404 and sitting 412 have significantly greater values than supine or prone. So for instance, assume that a first posture is established where the patient is either supine or prone 402, 410. Assume further that a pre-established threshold is established for Dmax of 105% to distinguish significant change from insignificant variations. If measured Dmax values increase to 105% or more of the values recorded in the first posture, then the technique can determine that the patient is undergoing (or just underwent) a posture change to sitting or standing where the thorax is generally vertical. If such Dmax values are detected, the technique proceeds to block 706, otherwise the technique returns to block 702.

Orthostatic hypotension therapy is administered at 706 in instances where the technique determines that the patient is standing-up. In one case, the orthostatic hypotension therapy constitutes increasing a pacing rate of the patient from a base pacing rate, such as 60 beats/minute to a higher pacing rate, such as 80 beats/minute. After a predefined period of time the pacing rate can be returned to the base pacing rate. Alternatively, the pacing rate can be restored to the base rate if the patient undergoes another posture change which eliminates the orthostatic hypotension incident. For instance, in a case where the patient is supine and stands up then lies back down orthostatic hypotension may be started and upon detecting that the patient has laid back down the orthostatic hypotension therapy can be discontinued. Various other orthostatic hypotension therapies should be recognized by the skilled artisan.

CONCLUSION

Although exemplary techniques, methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. An implantable medical device (IMD) comprising:
   a mechanism operative to sense IEGM data from a patient;
   a mechanism operative to determine patient postures from the IEGM data, the mechanism utilizing a parameter derived from the IEGM data and employing a ratio of values of the parameter sensed at different times to determine patient postures;
   a mechanism to provide patient therapy; and,
   a mechanism operative to alter patient therapy based upon the patient postures.

2. The IMD of claim 1, further comprising a mechanism for altering patient therapy based upon the detected patient posture change.

3. An implantable medical device (IMD) comprising:
   means for sensing IEGM data;
   means for determining from sensed IEGM data a patient posture;
   means for providing patient therapy; and,
   means for altering patient therapy based upon the posture;
   wherein the means for determining utilizes a parameter derived from the IEGM data and employs a ratio of values of the parameter sensed at different times to determine the patient posture.

4. The IMD of claim 3, wherein the means for determining is operable to distinguish a first posture where the patient's thorax is generally horizontal from a second posture where the patient's thorax is generally vertical.

5. The IMD of claim 3, wherein the means for determining is operable to detect a posture change from a first posture where the patient's thorax is generally horizontal to a second posture where the patient's thorax is generally vertical.

6. The IMD of claim 3, wherein the means for determining is normalized to a supine patient posture and is operable to distinguish posture changes from supine to right-side lying, supine to left-side lying, supine to prone, supine to sitting, and supine to standing.

7. The IMD of claim 3, wherein the means for altering inhibits delivery of patient therapy that may compromise the patient's balance when the patient's determined posture is a sitting posture or a standing posture.

8. The IMD of claim 3, wherein the patient therapy include delivery of shocking therapies.

9. An implantable medical device (IMD) comprising:
   means for sensing IEGM data;
   means for determining from sensed IEGM data a patient posture; and,
   means for providing patient therapy; and,
   means for altering patient therapy based upon the posture;

wherein the means for determining utilizes a parameter derived from the IEGM data and employs a ratio of values of the parameter to differentiate the posture from other patient postures.

10. The IMD of claim 9, wherein the means for determining utilizes multiple parameters derived from the IEGM data and employs a ratio of values of individual parameters to differentiate the posture from other patient postures.

11. A computer-implemented method comprising:

sensing intracardiac electrogram (IEGM) values from a patient;

monitoring the patient's activity level; and, in an instance where the patient's activity level exceeds a predetermined value, analyzing the sensed IEGM values to detect a patient posture change;

wherein the analyzing employs a ratio of sensed IEGM values sensed at different times to determine a patient posture change.

12. The computer-implemented method as recited in claim 11, wherein the analyzing comprises detecting a change in a single IEGM parameter that exceeds a pre-established threshold.

13. The computer-implemented method as recited in claim 11, wherein the analyzing comprises detecting changes in at least two different IEGM parameters that exceed pre-established thresholds established for the respective individual IEGM parameters.

14. The computer-implemented method as recited in claim 11 further comprising altering patient therapy based upon the detected patient posture change.

* * * * *